United States Patent [19]

Bailey

[11] 3,956,333

[45] May 11, 1976

[54] 1(OR 3)-PERFLUOROALKYL-3,4-DIHYDRO-2(1H)-ISOQUINOLINECARBONITRILES

[75] Inventor: Denis M. Bailey, East Greenbush, N.Y.

[73] Assignee: Sterling Drug Inc., New York, N.Y.

[22] Filed: June 19, 1975

[21] Appl. No.: 588,370

Related U.S. Application Data

[62] Division of Ser. No. 453,592, March 22, 1974, Pat. No. 3,927,000, which is a division of Ser. No. 282,266, Aug. 21, 1972, Pat. No. 3,855,228.

[52] U.S. Cl. .................................... 260/283 CN
[51] Int. Cl.$^2$ .................................... C07D 217/00
[58] Field of Search ............................ 260/283 CN

[56] References Cited
UNITED STATES PATENTS 3,505,336   4/1970   Bailey............................ 260/283 CN
3,637,709   1/1972   Houlihan et al................ 260/283 CN
3,769,291   10/1973  Parker et al.................... 260/283 CN

*Primary Examiner*—Alton D. Rollins
*Assistant Examiner*—David E. Wheeler
*Attorney, Agent, or Firm*—Robert K. Bair; B. Woodrow Wyatt

[57] ABSTRACT

(1-R- or 3-trifluoromethyl)-3,4-dihydro-2(1H)-isoquinolinecarboxamidoximes where R is pentafluoroethyl or heptafluoropropyl, having antithrombotic and antibacterial activities, are prepared by reacting the corresponding (1-R- or 3-trifluoromethyl)-3,4-dihydro-2(1H)-isoquinolinecarbonitriles which are prepared from the corresponding (1-R- or 3-trifluoromethyl)-3,4-dihydroisoquinolines via the (1-R- or 3-trifluoromethyl)-1,2,3,4-tetrahydroisoquinolines. Said tetrahydroisoquinoline where R is pentafluoroethyl also has antibacterial activity.

4 Claims, No Drawings

1(OR 3)-PERFLUOROALKYL-3,4-DIHYDRO-2(1H)-ISOQUINOLINECARBONITRILES

This application is a division of copending application Ser. No. 453,592, filed Mar. 22, 1974, and now U.S. Pat. No. 3,927,006 issued Dec. 12, 1975, which is a division of application Ser. No. 282,266, filed Aug. 21, 1972, and now U.S. Pat. No. 3,855,228, issued Dec. 17, 1974.

This invention relates to compositions of matter known in the art of chemistry as substituted-isoquinolines and to their preparation.

The invention sought to be patented, in a preferred composition aspect, resides in the compounds which I designate 1-(pentafluoroethyl)- or 1-(heptafluoropropyl)-3,4-dihydro-2(1H)-isoquinolinecarboxamidoxime of the formula I

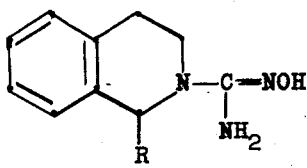

where R is pentafluoroethyl or heptafluoropropyl. Another composition aspect of the invention sought to be patented resides in 3,4-dihydro-3-(trifluoromethyl)-2(1H)-isoquinolinecarboxamidoxime of the formula II

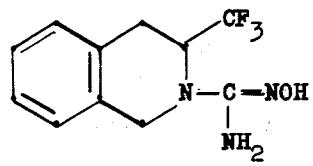

The compounds of said composition aspects of the invention have the inherent applied use characteristics of preventing thrombosis in mammalian species, thereby indicating their utility as antithrombotic agents. Also, these compounds have the inherent applied use characteristics of inhibiting growth of *Staphylococcus aureus*, thereby indicating their utility as antibacterial agents.

The above compounds of Formulas I and II are disclosed in said U.S. Pat. No. 3,855,228, issued Dec. 17, 1974.

The invention sought to be patented, in its process aspect, resides in the process of preparing said compounds of formulas I and II which comprises reacting the corresponding 1-(pentafluoroethyl)- or 1-(heptafluoropropyl)-3,4-dihydro-2(1H)-isoquinolinecarbonitrile of formula III or 3-trifluoromethyl-3,4-dihydro-2(1H)-isoquinolinecarbonitrile of formula IV

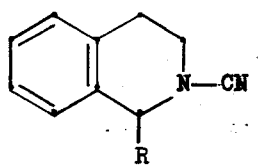

III

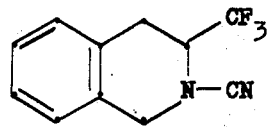

IV with hydroxylamine, where R is pentafluoroethyl or heptafluoropropyl.

Other composition aspects of the invention sought to be patented are said intermediates of formulas III and IV and other corresponding intermediates of formulas V and VI

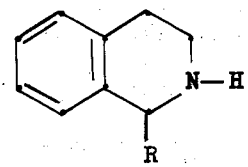

V

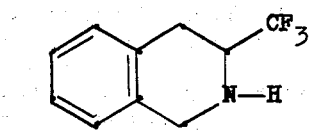

VI where R is defined as above in formulas I and III, the compound of formula V where R is pentafluoroethyl or heptafluoropropyl being, respectively, 1,2,3,4-tetrahydro-1-(pentafluoroethyl)isoquinoline or 1,2,3,4-tetrahydro-1-(heptafluoropropyl)isoquinoline and the compound of formula VI being 1,2,3,4-tetrahydro-3-trifluoromethylisoquinoline. The compound of formula V where R is pentafluoroethyl also has the inherent applied use characteristics of inhibiting growth of *Staphylococcus aureus*, thereby indicating its further utility as an antibacterial agent.

Other composition aspects of the invention sought to be patented are the intermediates of formulas VII and VIII

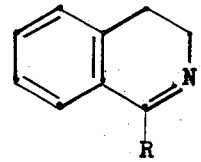

VII

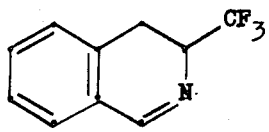

VIII where R is defined as in above formulas I, III and V, the compound of formula VII where R is pentafluoroethyl or heptafluoropropyl being, respectively, 3,4-dihydro-1-(pentafluoroethyl)isoquinoline or 1-heptafluoropropyl)-3,4-dihydroisoquinoline and the compound of formula VIII being 3,4-dihydro-3-(trifluoromethyl)isoquinoline. The compounds of formulas VII and VIII are useful in the preparation of the respective compounds of formulas V and VI, as shown hereinbelow.

The above intermediates of formulas V to VIII inclusive are disclosed and claimed in copending application Ser. No. 453,592, filed Mar. 22, 1974.

The 3,4-dihydro-2(1H)-isoquinolinecarboxamidoximes of formulas I and II, as well as the compounds of formulas V, VI, VII and VIII, are useful in the free base form or in the form of their acid-addition salts, and both forms are within the purview of the invention, and are considered to be one and the same invention. The acid-addition salts are simply a more convenient form for use; and, in practice, use of the salt form inherently amounts to use of the base form. The acids which can be used to prepare the acid-addition salts are preferably those which produce, when combined with the free base, pharmaceutically acceptable salts, that is, salts whose anions are relatively innocuous to the animal organism in pharmaceutical doses of the salts so that the beneficial properties inherent in the free base are not vitiated by side effects ascribable to the anions; in other words, the latter do not substantially affect the pharmaceutical properties inherent in the cations. Appropriate pharmaceutically acceptable salts within the scope of the invention are preferably those derived from mineral acids such as hydrochloric acid, hydrobromic acid, hydriodic acid, nitric acid, phosphoric acid, sulfamic acid and sulfuric acid; organic sulfonic acids such as methanesulfonic acid, ethanesulfonic acid, benzenesulfonic acid, p-toluenesulfonic acid and naponic acid (1,4-naphthalenedisulfonic acid); and other organic acids, e.g., salicyclic acid; and the like, giving: the hydrochloride, hydrobromide, hydriodide, nitrate, phosphate, sulfamate, sulfate, methanesulfonate, ethanesulfonate, benzenesulfonate, p-toluenesulfonate, naponate and salicylate, respectively.

The acid-addition salts are prepared preferably by reacting the free base and acid in an organic solvent, e.g., ethanol, 2-propanol, acetone, etc., in which case the salt separates directly or can be obtained by concentration of the solution.

The molecular structures of the 3,4-dihydro-2(1H)-isoquinolinecarboxamidoximes and corresponding intermediates of the invention are assigned on the basis of evidence provided by infrared (IR) and nuclear magnetic resonance (NMR) spectra, and, by the correspondence of calculated and found values for the elementary analyses for representative examples.

A particularly preferred embodiment of the invention is the compound of formula I where R is pentafluoroethyl, that is, 3,4-dihydro-1-(pentafluoroethyl)-2(1H)-isoquinolinecarboxamidoxime.

The manner of making and using our invention will now be generally described so as to enable the person skilled in the art of organic chemistry to make and use the same.

The 3,4-dihydro-2(1H)-isoquinolinecarboxamidoximes of formulas I and II are prepared by reacting the corresponding 3,4-dihydro-2(1H)-isoquinolinecarbonitrile (formulas III and IV) with hydroxylamine. The reaction is conveniently and preferably carried out by mixing the reactants in a suitable solvent at room temperature (about 25°–30°C.) and then heating (about 75°–100°C. or higher) if necessary. Suitable solvents are organic solvents, e.g., methanol, ethanol, dimethylformamide, tetrahydrofuran, and the like.

The intermediate 3,4-dihydro-2(1H)-isoquinolinecarbonitriles of formulas III and IV are prepared by the generally known method of reacting the corresponding 1,2,3,4-tetrahydroisoquinolines of formulas V and VI, respectively, with cyanogen bromide.

The intermediate 1,2,3,4-tetrahydro-1-R-isoquinolines of formula V are prepared by the generally known multi-step process of first reacting phenethylamine with an acylating agent, e.g., an acyl anhydride of the formula $(RCO)_2O$ or an acyl chloride of the formula RCOCl, to form the N-acyl compound of formula IX

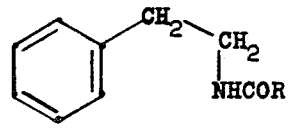

IX which on heating with a mixture of phosphorus oxychloride and phosphorus pentoxide ring closes to form the 1-R-3,4-dihydroisoquinoline of formula VII

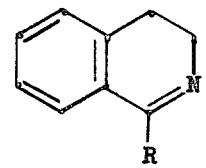

VII which, in turn, is catalytically hydrogenated using a suitable catalyst, e.g., platinum dioxide, to produce the corresponding 1,2,3,4-tetrahydro-1-R-isoquinoline of formula V where R is pentafluoroethyl or heptafluoropropyl.

The intermediate 1,2,3,4-tetrahydro-3-(trifluoromethyl)isoquinoline of formula VI is prepared by a series of reactions as follows:

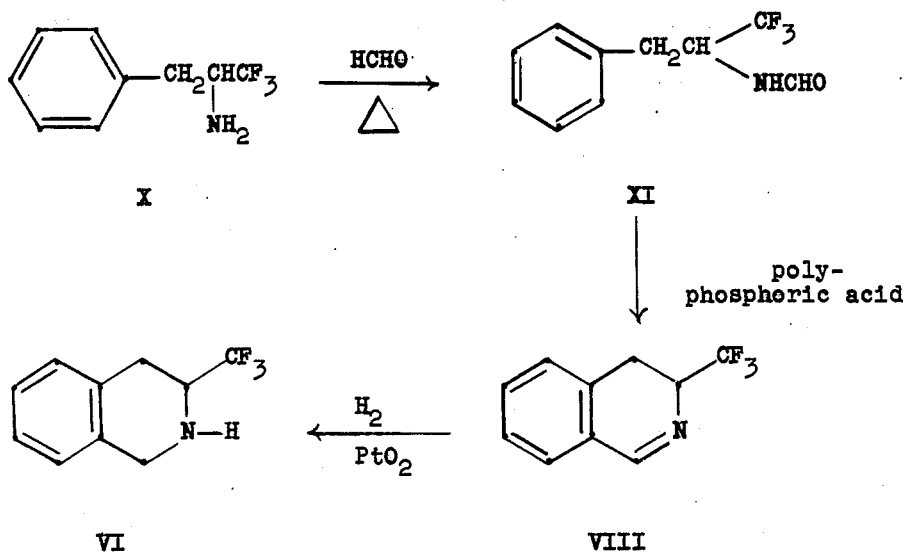

The intermediate 1,1,1-trifluoro-2-amino-3-phenylpropane (X) is a known compound.

The foregoing preparations are illustrated further hereinbelow.

The best mode contemplated for carrying out the invention are now being set forth, as follows.

EXAMPLE 1

A. N-(Phenethyl)-(pentafluoropropionamide) — A mixture containing 48 g. of phenethylamine and 50 ml. of triethylamine was added dropwise with stirring to a cooled solution containing 100 g. of pentafluoropropionic anhydride in 200 ml. of benzene. The mixture was stirred in an ice bath for thirty minutes and then poured into water. The aqueous mixture was extracted with ether. The ether extract was washed successively with sodium bicarbonate solution, brine, 2N hydrochloric acid and brine. The ether solution was then dried over anhydrous magnesium sulfate and the ether removed to yield 77 g. of N-(phenethyl)-(pentafluoropropionamide). A small sample was crystallized from n-hexane and dried in vacuo at 40°C. to yield the said compound, m.p. 79°–79.5°C.

B. 3,4-Dihydro-1-(pentafluoroethyl)isoquinoline — A mixture containing 120 g. of phosphorus pentoxide and 150 ml. of phosphorus oxychloride was heated to 70°–80°C. and to the stirred mixture was added 76 g. of N-(phenethyl)-(pentafluoropropionamide). The reaction mixture was heated to reflux whereupon it set up as a crystalline mass. To this mass was added another 130 ml. portion of phosphorus oxychloride and the mixture was heated at 150°C. with stirring whereupon it slowly became homogeneous. After the mixture had been heated for a total of five hours, the excess phosphorus oxychloride was distilled off in vacuo. The heat source was removed and water was added dropwise until the reaction subsided, a total of about one liter of water being added. The reaction mixture was cooled in an ice bath whereupon a crystallized solid separated. The solid was collected, washed with water and dried over phosphorus pentoxide at 0.1 mm. The compound was sublimed using a water bath at 40°–50°C. and a pressure of 0.5–1.0 mm. to yield 56.3 g. of 3,4-dihydro-1-(pentafluoroethyl)isoquinoline, m.p. 28°–29°C.

C. 1,2,3,4-Tetrahydro-1-(pentafluoroethyl)isoquinoline — A 45.8 g. sample of 3,4-dihydro-1-(pentafluoroethyl)isoquinoline was dissolved in absolute ethanol and the solution was diluted with ethanol to a volume of 200 ml. To the solution was added 1 g. of platinum dioxide and the mixture was subjected to catalytic hydrogenation until no more hydrogen was taken up. The catalyst was removed by filtration and the filtrate was concentrated in vacuo to remove the ethanol thereby yielding, as a pale orange oil, 45.5 g. of 1,2,3,4-tetrahydro-1-(pentafluoroethyl)isoquinoline. This compound was converted to the hydrochloride salt and the salt recrystallized from isopropyl alcohol-ether to yield 37.2 g. of 1,2,3,4-tetrahydro-1-(pentafluoroethyl)isoquinoline hydrochloride, m.p. 175°–178°C. after drying at 60°C. in vacuo.

D. 3,4-Dihydro-1-(pentafluoroethyl)-2(1H)-isoquinolinecarbonitrile — To a mixture containing 32.8 g. of sodium acetate in 250 ml. of methanol was added 30.0 g. of 1,2,3,4-tetrahydro-1(pentafluoroethyl)isoquinoline hydrochloride and the resulting mixture was stirred for ten minutes. To this stirred mixture kept below 25°C. was added dropwise over a thirty minute period a solution containing 15.9 g. of cyanogen bromide in 50 ml. of methanol. The reaction mixture was then kept overnight at room temperature (about 25°C.) The solvent was distilled off in vacuo at a temperature less than 35°C. and the remaining material was treated with a mixture of benzene and water. The layers were separated and the aqueous layer was extracted with benzene. The benzene layer and extract were combined and washed successively with water, saturated sodium bicarbonate solution and brine. The benzene solution was dried over anhydrous magnesium sulfate and the benzene removed in vacuo to yield an oil which crystallized. The crystalline product was recrystallized from 75 ml. of cyclohexane to yield 28.0 g. of 3,4-dihydro-1-(pentafluoroethyl)-2(1H)-isoquinolinecarbonitrile, m.p. 56°–57°C.

E. 3,4-Dihydro-1-(pentafluoroethyl)-2(1H)-isoquinolinecarboxamidoxime — To a stirred mixture containing 23.7 g. of 3,4-dihydro-1-(pentafluoroethyl)-2(1H)-isoquinolinecarbonitrile, 32 g. of anhydrous sodium carbonate and 100 ml. of dimethylformamide was added a solution containing 9 g. of hydroxylamine hydrochloride and 15 ml. of dimethylformamide. The resulting reaction mixture was stirred for two hours and filtered; the filter cake was washed with benzene. The combined filtrate and washings were poured into 1500 ml. of water and the mixture extracted with three 500 ml. portions of benzene. The combined benzene extracts were washed with three 300 ml. portions of water and then with a portion of brine. The benzene solution was extracted with four 200 ml. portions of 1N hydrochloric acid. The combined acidic extracts were washed with ether, cooled in an ice bath and made basic with 35% aqueous sodium hydroxide solution. The mixture was extracted with chloroform. The chloroform solution was dried over anhydrous magnesium sulfate and the chloroform distilled off in vacuo to yield, as an oil which crystallized, 22.6 g. of 3,4-dihydro-1-(pentafluoroethyl)-2(1H)-isoquinolinecarboxamidoxime. The crystalline product was mixed with 50 ml. of 2N hydrogen chloride in ethanol and the solvent removed in vacuo. To the residue was added 100 ml. of acetonitrile and the mixture heated to effect a solution. The product as its hydrochloride salt began to precipitate near the boiling point of the solvent and the mixture was allowed to cool to room temperature. The resulting precipitate was collected, washed with acetonitrile and dried in vacuo at 50°C. for three hours to yield 21.6 g. of 3,4-dihydro-1-(pentafluoroethyl)-2(1H)-isoquinolinecarboxamidoxime hydrochloride, m.p. 213°–215°C. with decomposition.

3,4-Dihydro-1-(pentafluoroethyl)-2(1H)-isoquinolinecarboxamidoxime in the form of its salicylate salt was prepared as follows. To a solution containing 0.93 g. of 3,4-dihydro-1-(pentafluoroethyl)-2(1H)-isoquinolinecarboxamidoxime in 20 ml. of ether was added a solution containing 0.414 g. of salicylic acid in 10 ml. of ether. The ether was distilled off in vacuo to yield a gummy material which was triturated with n-hexane and the mixture was cooled using a mixture of acetone and solid carbon dioxide. The solid which formed was collected, pulverized under n-hexane, collected again and dried at 35°C. and 0.1 mm. for 24 hours to yield 1.1 g. of 3,4-dihydro-1-(pentafluoroethyl)-2(1H)-isoquinolinecarboxamidoxime salicylate, m.p. 62°C. with previous shrinkage.

EXAMPLE 2

A. N-(Phenethyl)heptafluorobutyramide — To a cooled solution containing 30.25 g. of phenethylamine and 400 ml. of pyridine was added dropwise with stirring 100 g. of heptafluorobutyric anhydride. The reaction mixture was then allowed to warm to room temperature while stirring for a period of three hours. The mixture was then poured into 1500 g. of ice and stirred. The mixture was extracted with ether and the ether extract was washed successively with dilute hydrochloric acid and 10% potassium carbonate solution. The ether solution was then dried over anhydrous magnesium sulfate and the ether removed in vacuo. The remaining solid was recrystallized from ether-n-hexane to yield 69 g. of N-(phenethyl)heptafluorobutyramide, m.p. 56°–57°C.

B. 1-(Heptafluoropropyl)-3,4-dihydroisoquinoline, 56.3 g., b.p. 45°–47°C. at 0.075 mm., was prepared following the procedure described in Example 1B using 68.0 g. of N-(phenethyl)heptafluorobutyramide, 150 g. of phosphorus pentoxide and 500 ml. of phosphorus oxychloride.

C. 1-(Heptafluoropropyl)-1,2,3,4-tetrahydroisoquinoline hydrochloride, 50.2 g., m.p. 209°–210°C., was prepared following the procedure described in Example 1C using 48.0 g. of 1-(heptafluoropropyl)-3,4-dihydroisoquinoline, 2.0 g. of platinum oxide, 200 ml. of ethanol and recrystallization from ethanol-ether.

D. 1-(Heptafluoropropyl)-3,4-dihydro-2(1H)-isoquinolinecarbonitrile, 34.6 g., m.p. 67°–68°C., was prepared following the procedure described in Example 1D using 40 g. of 1-(heptafluoropropyl)-1,2,3,4-tetrahydroisoquinoline hydrochloride, 14.8 g. of cyanogen bromide, 32.8 g. of anhydrous sodium acetate, 300 ml. of methanol and recrystallization from ether-n-hexane.

E. 1-(Heptafluoropropyl)-3,4-dihydro-2(1H)-isoquinolinecarboxamidoxime, 15.25 g., m.p. 117°–118°C., was prepared following the procedure described in Example 1E using 34.3 g. of 1-(heptafluoropropyl)-3,4-dihydro-2(1H)-isoquinolinecarbonitrile, 31.8 g. of anhydrous sodium carbonate, 200 ml. of dimethylformamide, 14.7 g. of hydroxylamine hydrochloride and two recrystallizations from ether-n-hexane.

EXAMPLE 3

A. N-(1,1,1-Trifluoro-3-phenyl-2-propyl)formamide — A mixture containing 59 g. of 1,1,1-trifluoro-2-amino-3-phenylpropane and 100 ml. of formic acid (98%) was heated for three hours at 205°–215°C. The reaction mixture was allowed to cool and 68.6 g. of the solid product, N-(1,1,1-trifluoro-3-phenyl-2-propyl)formamide, was collected. A sample recrystallized from cyclohexane and dried in vacuo at 40°C. melted at 82°–82.5°C.

B. 3,4-Dihydro-3-(trifluoromethyl)isoquinoline — A mixture containing 300 g. of polyphosphoric acid and 60 g. of phosphorus pentoxide was heated at 160°–170°C. for 90 minutes. To the hot stirred mixture at 160°C. was added in portions 68 g. of N-(1,1,1-trifluoro-3-phenyl-2-propyl)formamide whereupon an exothermic reaction ensued, raising the temperature to about 170°C. The mixture was stirred for ninety minutes at 160°–170°C., cooled slightly and then poured into an excess of water. The aqueous acidic mixture was extracted with ether, and to the remaining acidic solution was added a piece of solid carbon dioxide; the solution was stored in a cold room overnight. Keeping the temperature of the acidic solution less than 30°C., solid potassium hydroxide was added to bring the pH to about 10 whereupon a solid separated. The solid was extracted with ether and benzene. The combined extracts were dried over anhydrous magnesium sulfate and the solvents removed in vacuo to yield 54 g. of 3,4-dihydro-3-(trifluoromethyl)isoquinoline. The solid was dissolved in 100 ml. of isopropyl alcohol and 100 ml. of water, and into the solution was passed dry hydrogen chloride. The resulting solid was collected to yield 55.4 g. of 3,4-dihydro-3-(trifluoromethyl)isoquinoline hydrochloride, m.p. 177°–179°C.

C. 1,2,3,4-Tetrahydro-3-(trifluoromethyl)isoquinoline hydrochloride, 30.5 g., m.p. (sublimes), was prepared following the procedure described in Example 1C using 37.1 g. of 3,4-dihydro-3-(trifluoromethyl)isoquinoline hydrochloride, 1 g. of platinum dioxide and enough absolute ethyl alcohol to bring the total reaction volume to 200 ml.

D. 3-(Trifluoromethyl)-3,4-dihydro-2(1H)-isoquinolinecarbonitrile, 20.2 g., was prepared following the procedure described in Example 1D using 20.7 g. of 1,2,3,4-tetrahydro-3-(trifluoromethyl)-isoquinoline hydrochloride in 150 ml. of methanol, 12.7 g. of cyanogen bromide in 60 ml. of methanol and 26.2 g. of sodium acetate. A sample recrystallized from cyclohexane melted at 61°–62°C.

E. 3,4-Dihydro-3-(trifluoromethyl)-2(1H)-isoquinolinecarboxamidoxime hydrochloride, 13.8 g., m.p. (indefinite), was prepared following the procedure described in Example 1E using 20 g. of 3-(trifluoromethyl)-3,4-dihydro-2(1H)-isoquinolinecarbonitrile, 9 g. of hydroxylamine hydrochloride, 31.8 g. of sodium carbonate, 150 ml. of dimethylformamide and recrystallization from isopropyl alcohol-n-hexane.

The antithrombotic activity of the compounds of formulas I and II of the invention was determined by standard in vitro and in vivo testing procedures described below.

The procedures used for determining in vitro the effectiveness of the compounds of the invention in blocking platelet aggregation caused by collagen or adenosine diphosphate (ADP) are described as follows.

Blood was collected for platelet aggregation studies as follows. Using siliconized plastic syringes containing 2.5 ml. of 3.8% trisodium citrate and siliconized 18 gauge needles, 25 ml. of blood was obtained from rabbits (unanesthetized New Zealand) by heart puncture. To prepare platelet-rich plasma (PRP) the citrated blood samples were poured into 50 ml. round-bottomed polycarbonate centrifuge tubes and centrifuged for ten minutes at 800 rpm (77 g.) in a Sorvall RC-2B refrigerated centrifuge (4°C.) using the SS-34 head. The PRP was transferred to 20 ml. round-bottomed polycarbonate tubes with siliconized Pasteur pipettes and kept in a water bath (20°–25°C.). Platelet-poor plasma (PPP) was prepared by centrifugation of 2 ml. PRP for ten minutes at 3400 rpm in the Sorvall centrifuge at 4°C. For in vitro studies PRP was pooled but for in vivo studies PRP from individual animals was tested.

Platelet aggregation in PRP was determined by the photometric method of Born as modified by Mustard et al. [J. Lab. Clin. Med. 64, 548 (1964)]. A one ml. sample of PRP was transferred with a plastic pipette to a flat-bottomed cuvette (10.5 mm. I.D., 60 mm. long) containing an iron stir bar 8 mm. long. The cuvette was placed in the temperature controlled cell compartment of a Model 201S Bryston Aggregometer where stirring was achieved from below by a magnetic stirrer. The aggregometer controls were adjusted so that the plasma specimen was stirred at 1100–1500 rpm and 37° ± 1.9°C. Transmittance of light from a tungsten lamp through the cuvette to a photoelectric cell was recorded on a Bausch and Lomb V.O.M. -5 recorder at 10 millivolts full scale sensitivity. Minimum transmittance (baseline) was set at 1 millivolt using platelet-rich plasma; maximum transmittance was set at 9 millivolts using a platelet-poor plasma blank.

Platelet aggregation was induced by the addition of 0.1 ml. aliquots of ADP or collagen. The final concentrations of the aggregating agents were chosen so that they produced a just maximal effect and usually were: (1) ADP-10 $\mu$M; (2) collagen — that concentration achieved by adding stock solution diluted 1:3.

When tested by the above-described in vitro procedures, 3,4-dihydro-1-(pentafluoroethyl)-2(1H)-isoquinolinecarboxamidoxime hydrochloride (Example 1E), 1-(heptafluoropropyl)-3,4-dihydro-2(1H)-isoquinolinecarboxamidoxime (Example 2E) and 3,4-dihydro-3-(trifluoromethyl)-2(1H)-isoquinolinecarboxamidoxime hydrochloride (Example 3E) were found to produce the following % inhibition of platelet aggregation at the indicated dose levels (M = molar):

In vitro Inhibition of Platelet Aggregation
Platelet Aggregation Induced by

| Compound | ADP Effective Conc. | % Inhibition | Collagen Effective Conc. | % Inhibition |
|---|---|---|---|---|
| Example 1E | 3×10⁻³M | 74.2 | 1×10⁻⁴M | 24.3 |
| Example 2E | 1×10⁻³M | 8.3 | 1×10⁻³M | 94.2 |
| Example 3E | 3×10⁻³M | 64.4 | 3×10⁻⁴M | 67.4 |

The antithrombotic or platelet aggregation inhibitory effect of the compounds of formulas I and II was further determined by a modified extracorporeal shunt technique in rabbits. Rowntree and Shinoya [J. Exp. Med. 46, 7 (1927)] described a method of extracorporeal circulation for the observation of thrombus formation. Downie et al. [Circulation Res. 12, 441 (1963)] modified this technique in order to study the effects of various chemicals upon the platelet aggregates formed in such a system. The following procedure, a further modification of said technique, was used to determine the antithrombotic activity of the compounds of the invention.

New Zealand rabbits weighing 1.5 to 3.0 kg. each were used for these studies. All animals were dosed orally by stomach tube with the test compound at a given time, e.g., 3, 8, 12, 24, etc. hours, prior to testing the blood samples. Control animals (from 3 to 5 in number for each dose level of compound) were given the vehicle used for solubilizing the compounds tested. All animals were anesthetized with sodium pentobarbital (Pentobrocanal) intravenously, 25–32 mg./kg., and secured to a dissecting board. The right femoral artery was cannulated and connected to a Statham pressure transducer (P 23AC) for continuously measuring arterial blood pressure which was recorded by means of a Grass (Model 7) polygraph.

A longitudinal incision was made in the midcervical region. The jugular vein and the carotid artery on one side were isolated and cannulated with appropriate size catheters filled with saline solution, which were in turn connected via Y-shaped polypropylene connectors establishing the shunt.

The components of the shunt were thoroughly siliconized except for the Y-connector on the arterial side. This connector is weighed prior to running the experiment. A blood sample was withdrawn from the femoral artery to provide a control platelet count. The animal was allowed 10–12 minutes to attain a relatively stable blood pressure level after which the shunt was opened and the blood permitted to flow. The time from the first appearance of blood in the arterial catheter until its re-entry into the body, via the venous catheter, was measured and recorded, as flow time, which was used to determine the initial rate of flow.

The shunt remained open for a period of twenty minutes. One minute before the end, the femoral catheter was removed from the transducer and a second blood sample was taken. Duplicate platelet counts were made for each sample of blood. The shunt was removed from the animal by pulling out both catheters, arterial and venous, arterial first. The Y-connectors were washed with 10 cc. of saline solution. The arterial Y-connector was separated and dried in an oven overnight at 40°C., then reweighed. The initial weight of the connector was subtracted from the final weight, and the difference is considered to be the mass of the platelet aggregate (thrombus).

After the rabbits were anesthetized in preparation for the shunt technique, bleeding times were determined. An area of the inner thigh of the animal was prepared by gently clipping the hair with a scissors and washing the area. The area was not scrubbed to prevent hyperemia which produces false bleeding times. A magnifying lens and light were positioned over the area to be examined. A small quick incision 1 cm. long was made in the skin. A stop watch was started as the severed subcutaneous vessels started bleeding. As soon as the cut was made, saline solution was slowly dripped (1 drop/2sec.) from an infusion bottle above the incision area so that it gently washed away the blood from the cut vessels. The primary bleeding time was noted and the vessels were observed for up to twenty minutes for re-bleeding and time of secondary bleeding was noted if it was seen. Duplicate readings (one from each thigh) were made on all animals.

When tested by the foregoing in vivo procedure, 3,4-dihydro-1-(pentafluoroethyl)-2(1H)-isoquinolinecarboxamidoxime hydrochloride (Example 1E) was found to produce the following % inhibition of platelet aggregation at oral dose levels of 50, 25 and 10 mg./kg. (single dose medication), the blood samples having been tested three hours after medication:

| | In vivo Inhibition of Platelet Aggregation by the Compound of Example 1E | | |
|---|---|---|---|
| | 50 mg/kg | 25 mg/kg | 10 mg/kg |
| $\bar{x}$ Deposit Weight ± s.d. | 1.08 ± 0.08 | 1.16 ± 0.05 | 1.54 ± 0.09 |
| % Inhibition | 41% | 38% | 17% |
| $P^a$< | 0.0005 | 0.0005 | 0.0005 |
| $\bar{x}^b$ Bleeding time ± s.e. | 506±7$^c$ | 548±9 | 405±8 |

$^a$P = probability factor.
$^b\bar{x}$ = mean.
$^c$506±7 means 5 minutes, 6 seconds ± 7 seconds.

The antibacterial activities for the compounds of formulas I and II and the compound of formula V where R is pentafluoroethyl were established using standard serial dilution techniques as described by Goss and Cimijotti, Applied Microbiology 16, 1414 (1968). The minimal (bacteriostatic) inhibitory concentrations (MIC) of said compounds thus tested against Staphylococcus aureus were found to be in the range of about 60 to 250 mcg./ml. for the compounds of formulas I and II and about 500 mcg./ml. for the compound of formula V where R is pentafluoroethyl.

The actual determination of the numerical biological data definitive for a particular compound of the invention is readily obtained according to the above standard test procedures, by technicians versed in pharmacological or bacteriological test procedures, without any need for any extensive experimentation.

The compounds of the invention can be prepared for use by conventional pharmaceutical procedures: that is, by dissolving or suspending them in a pharmaceutically acceptable vehicle, e.g., water, aqueous alcohol, glycol, oil solution or oil-water emulsions, for oral or parenteral administration; or by incorporating them in unit dosage form as tablets or capsules for oral administration either alone or in combination with suitable adjuvants such as calcium carbonate, starch, lactose, talc, magnesium stearate, gum acacia, and the like. When used as antithrombotic agents, they are preferably formulated and used orally, although other routes of administration, e.g., intramuscularly and intravenously, can be used.

I claim:
1. A compound selected from the group consisting of 3,4-dihydro-1-(pentafluoroethyl)-2(1H)-isoquinolinecarbonitrile, 1-(heptafluoropropyl)-3,4-dihydro-2(1H)-isoquinolinecarbonitrile and 3,4-dihydro-3-(trifluoromethyl)-2(1H)-isoquinolinecarbonitrile.
2. 3,4-Dihydro-1-(pentafluoroethyl)-2(1H)-isoquinolinecarbonitrile according to claim 1.
3. 1-(Heptafluoropropyl)-3,4-dihydro-2(1H)-isoquinolinecarbonitrile according to claim 1.
4. 3,4-Dihydro-3-(trifluoromethyl)-2(1H)-isoquinolinecarbonitrile according to claim 1.

* * * * *

UNITED STATES PATENT AND TRADEMARK OFFICE
CERTIFICATE OF CORRECTION

PATENT NO. : 3,956,333
DATED : May 11, 1976
INVENTOR(S) : Denis M. Bailey

It is certified that error appears in the above-identified patent and that said Letters Patent are hereby corrected as shown below:

Column 1, line 8, "3,927,006" should read -- 3,927,000 --; and, "Dec. 12," should read -- Dec. 16, --.

Signed and Sealed this

Fifth Day of October 1976

[SEAL]

Attest:

RUTH C. MASON
Attesting Officer

C. MARSHALL DANN
Commissioner of Patents and Trademarks